United States Patent [19]

Solem et al.

[11] Patent Number: 4,854,318

[45] Date of Patent: Aug. 8, 1989

[54] BLOOD VESSEL HOLDER AND METHOD OF USING IN ANASTOMOSIS

[75] Inventors: Jan O. Solem, Bjarred; Christian Olin, Lund, both of Sweden; Timothy M. Scanlan, St. Paul, Minn.

[73] Assignee: Scanlan International, St. Paul, Minn.

[21] Appl. No.: 135,146

[22] Filed: Dec. 18, 1987

[51] Int. Cl.⁴ .................. A61B 17/00; A61B 17/28
[52] U.S. Cl. ................................ 128/346; 128/321
[58] Field of Search ............ 128/334 R, 346, 359, 128/354, 321; 294/19.1, 99.2

[56] References Cited

U.S. PATENT DOCUMENTS

| | | | |
|---|---|---|---|
| 1,795,256 | 3/1931 | Johnson | 292/99.2 |
| 3,321,736 | 5/1967 | Flynn | 294/99.2 |
| 4,165,747 | 8/1979 | Bermant | 128/346 |
| 4,446,866 | 5/1984 | Davison | 128/321 |
| 4,484,581 | 11/1984 | Martin et al. | 128/346 |
| 4,484,911 | 11/1984 | Berlin et al. | 128/346 |

OTHER PUBLICATIONS

Plastics World "LEXAN Resin" Feb. 1985, pp. 28, 29.

Primary Examiner—Edward M. Coven
Assistant Examiner—Gary Jackson
Attorney, Agent, or Firm—Faegre & Benson

[57] ABSTRACT

A device for maintaining an opening in a first blood vessel in open position during a surgical procedure for suturing the opening in the first blood vessel to an opening in a second blood vessel. The device comprises: an elongate slender barrel with a straight longitudinal axis from the handle end to the tip end, a groove extending the length of the barrel, the groove ending in a slanting open cavity at the tip end, and a leaf spring clamp attached to the barrel to clamp the blood vessel to the posterior convex surface of the tip.

19 Claims, 1 Drawing Sheet

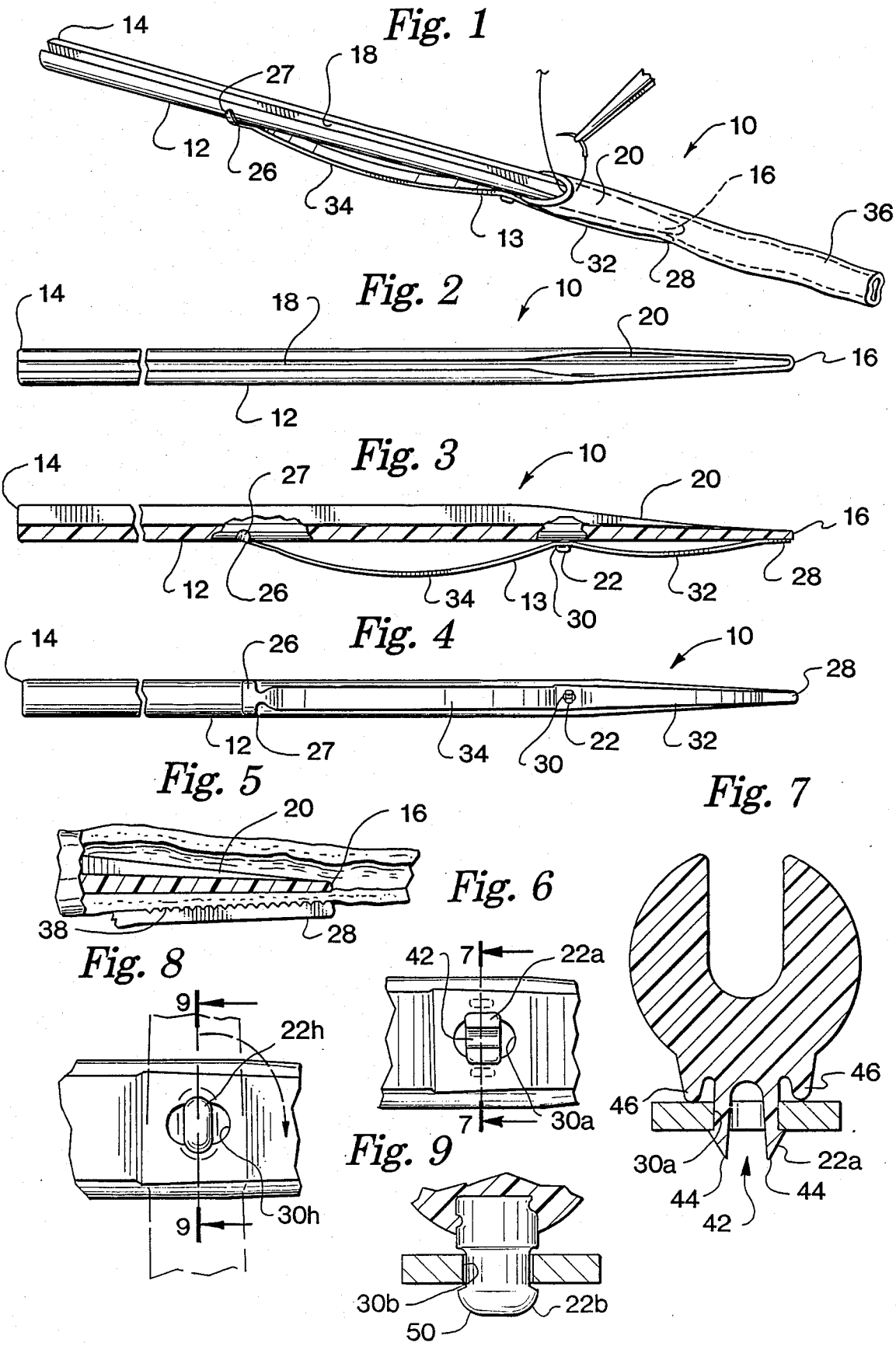

BLOOD VESSEL HOLDER AND METHOD OF USING IN ANASTOMOSIS

BACKGROUND OF THE INVENTION

1. Field of the Invention

This invention relates to a surgical device for holding an opening in a blood vessel in open position and to a method of using this device for holding an opening in a first blood vessel in position for anastomosis to an opening in a second blood vessel during a surgical procedure.

The blood vessel holder of this invention is especially suited for maintaining an opening in a first blood vessel in position for suturing to an opening in another blood vessel, for example in anastomosing an open-ended vein to a side opening in the aorta or one of its branches. Side-to-side and end-to-end anastomoses may also be performed with this blood vessel holder. This blood vessel holder is also suited for use in joining sections of other tubular bodily structures, e.g. bowel, fallopian tubes, etc. The present blood vessel holder is particularly suited for use during coronary bypass and peripheral vascular surgery. The blood vessels or other tubular bodily structures may be of biological or synthetic origin.

2. Description of the Prior Art

In procedures where the opening blood vessel is to be joined to the opening in a second blood vessel, such holding devices as forceps have commonly been used to maintain the first blood vessel in position while sutures to the second blood vessel are placed. It is easy for the blood vessel or forceps to slip, and the wall of the blood vessel is susceptible to traumatic damage. In attempting to overcome the problems inherent to the use of forceps in such procedures, a number of blood vessel holding devices have been proposed.

The Huang vein holder, available from Codman and Shurtleff, Incorporated, Randolph, Mass., presents a slender hollow tubular handle with an open tapering tip at one end for insertion into the open end of a blood vessel to maintain it in position for anastomosis. To secure the blood vessel to the Huang vein holder, an eye hook is provided on the exterior of the tubular handle at the base of the open tapering tip. The Huang vein holder is cumbersome to use, as it requires a suture to be placed each time the blood vessel is applied to the holder. This unduly lengthens the surgical procedure, because of the time and care required for placement and removal of such sutures.

Suma, et al describe a vein holder for coronary bypass surgery in *Ann. Thorac. Surg.* 43:109–110, January 1987. Their vein holder for distal (vein graft-to-coronary artery) anastomosis is constructed with an outer sheath and inner shaft. The outer sheath is constructed for insertion into the lumen of a vein graft. The inner sheath has three linear pins at the end of the shaft that expand when the outer sheath is slid back, so as to hold the incision open by expanding the vein. Their vein holder for proximal (vein graft-to-aorta) anastomosis has a bullet-shaped hollow body and perpendicular flat arm. Neither of these vein holders provide any Positive feature for contact with the exterior of the vein to securely hold the vein in position, and thus slippage and collapse of the vein is possible during the anastomosis procedure.

U.S. Pat. No. 4,651,731, issued Mar. 24, 1987 to Mobin-Uddin describes a surgical blood vessel holding device having a shank means in a middle region with a handle at one end and a narrow prong at the other end. The prong is provided with a hook extending laterally from the side thereof. The prong is adapted to be inserted into the open end of a blood vessel until the hook reaches the distal end of the vessel. The hook then pierces the vessel wall allowing the device to dispose the end of the blood vessel in facing relationship with respect to an opening in the wall of another blood vessel. The blood vessel can be locked onto the hook. A few sutures are then taken to hold the two blood vessels in facing relationship. The prong is then unhooked, removed, and suturing is completed. This device is susceptible to mispositioning during use. The vein, once hooked into position can easily slip off the hook if tension is slightly reduced. The amount of tension to be applied requires extreme practice and coordination. The longitudinally slidable locking clip which may be provided to reduce the possibility of slippage pinches the vein and may cause undue trauma thereto. This device is thus extremely tedious and difficult to use.

The design and function of the blood vessel holding device of this invention is intended to obviate the various problems associated with the use of these previously available blood vessel holders.

SUMMARY OF THE INVENTION

The blood vessel holding device of this invention comprises:

An elongate, slender barrel having a distal butt end and a proximal bill tip end, a longitudinal groove extending the length of the barrel, the groove terminating in a slanting open cavity at the proximal bill tip end of the barrel, and a clamp attachment means on the exterior of the barrel; and Clamping means attached to the barrel by the clamp attachment means, the clamping means being substantially coterminous with the proximal tip of the barrel.

The blood vessel holder is designed to be grasped by the elongate barrel with the slanting open cavity at the proximal end of the barrel available for insertion into the opening of a blood vessel. The elongate slender shape of the barrel is designed to provide sufficient length to the instrument to facilitate reaching deep cavity areas within the body.

The slanting open cavity at the proximal end of the barrel is designed for insertion into the opening in the blood vessel. The slanting open cavity of the barrel may desirably be designed with a thinner wall construction then the longitudinal groove of the barrel to further facilitate its insertion into the opening of the blood vessel and to further serve to maintain the opening and the blood vessel in open position during the anastomosis procedure. The proximal bill tip end of the barrel and the edges of the open cavity are preferably smooth and rounded to facilitate insertion into the opening of the blood vessel and to minimize trauma and damage thereto.

The clamping means is designed to provide secure atraumatic retention of the opening of the blood vessel on the proximal bill tip end of the barrel during the initial placement of sutures to an opening in a second blood vessel. Preferably, the clamping means is designed as an elongate, slender leaf spring clamp having a distal barrel alignment end and a clamping proximal end. The leaf spring clamp is preferably releasably attached to the barrel in longitudinal alignment therewith by the clamp attachment means on the barrel. The proximal end of the leaf spring clamp is substantially coterminous with the proximal bill tip end of the barrel and is designed to maintain a spring releasable clamping relationship therewith for retaining the wall of the blood vessel securely and atraumatically against the bill tip end of the barrel. The distal end of the spring clamp extends toward the distal end of the barrel and is designed to further maintain the leaf spring clamp in longitudinal alignment with the barrel. The clamping end of the leaf spring clamp may further be provided with transverse teeth to further facilitate securely retaining the wall of the blood vessel against the tip end of the barrel.

The attachment of the leaf spring clamp to the barrel by the clamp attachment means may be of any form which will facilitate maintaining the leaf spring and the barrel in longitudinal alignment with each other, while also allowing the proximal end of the leaf spring to maintain a releasable clamping relationship with the tip end of the barrel. For example, the leaf spring may be provided with an opening hole and the clamp attachment means may be designed as a locking button to retain the leaf spring through this opening hole either by a pivoting attachment, by a snap attachment or by any other suitable means. Alternatively, other means of attaching the clamping means to the barrel may be used, so long as secure, atraumatic and readily releasable clamping means are used. Thus, the clamping means, such as the leaf spring, may be permanently attached to the barrel and may, if desired, be manufactured as one piece with the barrel of the blood vessel holder.

In using the blood vessel holder of this invention, the holder is grasped manually by the barrel and the clamping means is released. The proximal end of the blood vessel holder, that is the slanting open cavity at the proximal bill tip end of the barrel, is inserted into the interior lumen of a first blood vessel through the opening thereof, preferably a "fish-mouth" opening. The first blood vessel is slid up the slanting open cavity until the opening of the blood vessel can be supported and maintained in open position by the slanting open cavity. Thereupon, the clamping means is secured to maintain the first blood vessel in proper position on the holder. The opening of the first blood vessel is then aligned adjacent to an opening in a second blood vessel.

A suture is placed between the first blood vessel and the second blood vessel while the first blood vessel is being secured by the holder. Several loose sutures can be placed to assure proper alignment between the openings of the two blood vessels. After a sufficient number of sutures have been taken, the clamping means is again released to release the first blood vessel. The blood vessel holder can then be removed and laid aside. The anastomosis procedure is then completed by tightening the loosely applied sutures and adding additional sutures as needed.

The blood vessel holding device of this invention aids in the initiation of the anastomosis by securely maintaining the opening of the blood vessel in the desired open position. The slanting open cavity of the barrel maintains the walls of the blood vessel against collapse and also provides a firm surface against which the needle can press in application of the sutures.

As the anastomosis procedure is carried out, the opening of the blood vessel is initially supported by the blood vessel holder and subsequently by sutures as they are applied. Greater visibility and ease of suturing is facilitated by the use of this holder allowing the suturing procedure to be completed in a shorter period of time, with greater precision and with less trauma to the involved blood vessels and surrounding tissue.

BRIEF DESCRIPTION OF THE DRAWINGS

FIG. 1 is a perspective view of the blood vessel holder of this invention;

FIG. 2 is a top plan view showing the longitudinal groove and the slanting open cavity;

FIG. 3 is a right side elevational view of the holder with parts broken away;

FIG. 4 is a bottom plan view further illustrating an embodiment of the clamping means;

FIG. 5 is a fragmentary right side elevational detail of the tip end of the holder with a vein held in clamped position, shown with parts broken away;

FIG. 6 is a bottom plan view of the clamp attachment means shown as a locking button adapted for snap attachment of the leaf spring clamp;

FIG. 7 is a sectional elevational view taken along line 7—7 in FIG. 6 illustrating in greater detail the snap locking button attachment;

FIG. 8 is a fragmentary bottom plan view of a clamp attachment means in alternate form, adapted for pivotally attaching the clamping means to the barrel; and FIG. 9 is a sectional elevational view taken along line 9—9 of FIG. 8.

DETAILED DESCRIPTION OF THE PREFERRED EMBODIMENT

FIG. 1 shows a blood vessel holder 10 which may be formed of metal, such as stainless steel, or molded of a synthetic resin, such as polycarbonate. The blood vessel holder 10 is generally straight, slender and elongated, and comprises an elongate slender barrel 12 and a clamping means. As shown in FIG. 1, the clamping means may be leaf spring clamp 13 maintained in longitudinal alignment with the barrel 12. The elongate slender barrel 12 has a distal butt end 14 and a proximal bill tip end 16, and a longitudinal groove 18 extending the length of the barrel 12 from the distal butt end 14 to the proximal bill tip end 16. The purpose of the groove is to facilitate efficient manufacturing of the blood vessel holder, by providing for ease of molding and release from the mold. The blood vessel holder may be designed without the groove 18 if desired. The barrel 12 has a protracted slant at the proximal bill tip end 16, with the groove 18 forming an extended slanting open cavity 20 at the proximal bill tip end of the barrel 12. The edges of the bill tip end 16 are smooth and rounded.

A clamp attachment means is provided on the barrel 12 for attachment of the clamping means. Preferably, the clamp attachment means is a locking button 22 provided on the exterior of the barrel 12 opposite the longitudinal groove 18 at the slanting open cavity 20. The leaf spring clamp 13 has a distal barrel alignment end 26 and a proximal clamping end 28. The leaf spring clamp 13 is attached to the barrel 12 in longitudinal alignment therewith by means of the locking button 22 on the barrel 12. The distal barrel alignment end 26 of the leaf spring clamp 13 is suitably provided with means to maintain the leaf spring clamp 13 in longitudinal alignment with the barrel 12, for example by means of a follower 27 which generally conforms to the circumference of the barrel 12. The proximal clamping end 28 of the leaf spring clamp 13 is substantially coterminous with the proximal bill tip end 16 of the barrel 12. The attachment of the leaf spring clamp 13 to the locking button 22 may be facilitated by any means which will serve to maintain the leaf spring clamp in longitudinal alignment with the barrel 12 while also serving to maintain the proximal clamping end 28 of the leaf spring clamp 13 in spring releasable clamping relationship with the bill tip end of the barrel 16. For example, the leaf spring clamp may be provided with a hole opening 30 which pivotally attaches to the button 22, or more preferably the locking button may be designed as shown in FIGS. 6 and 7 which provides for a secure snap attachment of the hole 30 of the leaf spring clamp 13 to the button 22 of the barrel 12. As further illustrated in FIG. 1, the protracted slanting open cavity 20 serves to support and maintain the open end of a blood vessel in proper position for anastomosing to a second blood vessel, not shown. The clamping means, such as the illustrated leaf spring clamp 13, may be formed of metal, such as stainless steel, or molded of a synthetic resin, such as polycarbonate.

FIG. 2 shows a top plan view of the blood vessel holder 10, illustrating the interior of the longitudinal groove 18 and the interior of the protracted slanting open cavity 20 at the proximal bill tip end 16 of the barrel 12. The edges of the proximal bill tip end 16 of the barrel 12 and the edges of the protracted slanting open cavity 20 are smooth and rounded to facilitate easy insertion into the open end of a blood vessel.

FIG. 3 is a right side elevational view of the blood vessel holder of this invention with parts broken away, further illustrating an embodiment of the holder where the clamping means is a slender, elongated leaf spring clamp 13 and the clamp attachment means is a locking button 22. As illustrated both the spring jaw 32 between the proximal clamping end 28 and the locking button 22 and also the span 34 between the locking button 22 and distal end of the clamp 26 are bowed away from the surface of the barrel 12. The proximal clamping end 28 preferably conforms to the surface of the barrel 12 at the tip portion 16 thereof. In use, pressure on the span 34 releases the proximal clamping end 28 of the leaf spring clamp 13 away from the bill tip end 16 of the barrel 12 to allow for inserting the blood vessel holder 10 into the open end of a blood vessel 36. Once the open cavity 20 of the barrel 12 has been inserted into the blood vessel 36 a suitable distance to maintain the blood vessel in open position, pressure on the span 34 is released, thus allowing the proximal clamping end 28 of the leaf spring clamp 13 to securely engage the wall of the blood vessel 36 against the tip end of the barrel 16.

It will be obvious to those skilled in the art, that any means of clamping the blood vessel 36 to the proximal bill tip end 16 of the barrel may be used, so long as secure, atraumatic, and easily releasable clamping means are used. Thus, the clamping means, such as the leaf spring, may be permanently attached to the barrel 12 and may, if desired, be manufactured in one piece with the barrel.

FIG. 4 is a bottom plan view showing the leaf spring clamp 13 maintained in longitudinal alignment with the barrel 12 by means of the locking button 22 and the follower 27 and with the proximal clamping end 28 of the leaf spring clamp 13 in clamping engagement with the bill tip end 16 of the barrel 12.

FIG. 5 is a fragmentary right side elevational detail of the tip end of the blood vessel holder retaining a blood vessel securely in place with parts broken away and shown slightly enlarged from the illustrations in FIGS. 1 through 4. A blood vessel 36 prepared with a fishmouth opening has been drawn up over the protracted slanting open cavity 20. Preferably, the proximal clamping end 28 of the leaf spring clamp 13 is provided with teeth 38 to facilitate secure atraumatic engagement of the blood vessel 36.

FIG. 6 is a bottom plan view of the clamp attachment means, illustrated as a preferred embodiment, a locking button 22a adapted for snap attachment of the clamping means. FIG. 7 is a sectional elevation taken along line 7—7 in FIG. 6 illustrating in greater detail the snap locking button attachment greatly enlarged from the view in FIG. 6. As illustrated in FIG. 7, the locking button 22a is comprised of a forked retainer 42 of two flexible barbs 44a and 44b and two pivots 46a and 46b. The clamping means is provided with a hole 30a sized to snap fit with the flexible barbs 44a–44b, while the pivots 46a–46b support the clamping means. Preferably the clamping means is a leaf spring clamp 13.

FIG. 8 is a fragmentary bottom plan view of a clamp attachment means in alternate form, as a locking button 22b adapted for pivotally attaching the clamping means to the barrel. The locking button 22b, as shown in FIG. 9, is generally oval in outline and terminates in an expanded swell 50. The clamping means is provided with a hole 30b of substantially the same generally oval outline as the locking button 22b. The hole 30b and the locking button 22b are oriented relative to each other such that the hole 30b fits over the locking button 22b, and allows the clamping means to pivot into a locking longitudinal alignment with the barrel 12. The clamping means is preferably a leaf spring clamp 13.

Although the present invention has been described with reference to preferred embodiments, workers skilled in the art will recognize that changes may be made in form and detail without departing from the spirit and scope of the invention.

What is claimed is:

1. A blood vessel holder comprising:
   an elongate slender barrel having a substantially straight longitudinal axis from a distal handle end to a proximal tapered open cavity tip, for insertion into an opening in a blood vessel; and
   a clamping means in clamping alignment with the barrel convex surface of said cavity for providing secure, atraumatic, releasable attachment of the opening of the blood vessel to the proximal tip posterior convex surface.

2. The blood vessel holder according to claim 1, wherein the clamping means is attached to the barrel by a barrel attachment means.

3. A blood vessel holder according to claim 2, wherein the barrel attachment means is a locking button and the clamping means is a leaf spring clamp.

4. A blood vessel holder according to claim 3, wherein the blood vessel holder is polycarbonate or stainless steel.

5. A blood vessel holder according to claim 1, wherein the barrel is provided with a longitudinal groove extending the length of the barrel to the distal end to the proximal tip, the groove opening out to form the protracted slanting open cavity at the proximal tip of the barrel.

6. The blood vessel holder according to claim 1, wherein the clamping means is substantially coterminous with the proximal tip of the barrel in spring releasable clamping relationship therewith for retaining the opening of the blood vessel.

7. A blood vessel holder according to claim 1, wherein the edges of the proximal tip and the protracted slanting open cavity are rounded.

8. The blood vessel holder according to claim 3, wherein the proximal clamping end of the leaf spring clamp is provided with securing teeth.

9. A blood vessel holder according to claim 3, wherein the leaf spring clamp attaches to the barrel by means of a pivot locking button, the barrel is polycarbonate and the locking button and the spring clamp are stainless steel.

10. The blood vessel holder according to claim 3, wherein the leaf spring clamp attaches to the barrel by means of a snap locking button, the barrel and the locking button are molded of polycarbonate and the spring clamp is stainless steel.

11. A tubular body structure holder comprising:
an elongate slender barrel having a substantially straight longitudinal axis extending from a distal handle end to a proximal tapered open cavity tip for insertion into an opening in a tubular body structure;
a clamping means in clamping alignment with the barrel convex surface of said open cavity for providing secure, atraumatic, releasable attachment of the opening of the tubular body structure to the proximal tip posterior convex surface.

12. The holder according to claim 11 wherein the clamping means is attached to the barrel by a barrel attachment means.

13. The holder of claim 11 wherein the clamping means is a leaf spring clamp and the barrel attachment means is a locking button.

14. The holder of claim 11 wherein edges of the proximal tip and the protracted slanting open cavity are rounded.

15. The holder of claim 11 wherein the barrel is polycarbonate and the clamping means is stainless steel.

16. A blood vessel holder comprising:
a barrel having a substantially straight longitudinal axis from a distal end to a proximal tip end, an open cavity slanting to the proximal tip end of the barrel for insertion into an opening in a blood vessel;
a clamping means in clamping alignment with the barrel convex surface of said open cavity for releasably securing an opening in a blood vessel to the proximal tip posterior convex surface.

17. The holder of claim 16 wherein the clamping means is a leaf spring clamp attached to the barrel by a barrel attachment means.

18. The holder of claim 16 wherein the barrel is polycarbonate and the clamping means is stainless steel.

19. The holder of claim 16 wherein edges of the proximal tip end of the barrel and the slanting open cavity are rounded.

* * * * *